(12) United States Patent
Järverud

(10) Patent No.: US 8,498,702 B2
(45) Date of Patent: Jul. 30, 2013

(54) IMPLANTABLE MEDICAL DEVICE AND METHOD FOR MONITORING SYNCHRONICITY OF THE VENTRICLES OF A HEART

(75) Inventor: Karin Järverud, Solna (SE)

(73) Assignee: St. Jude Medical AB, Jarfalla (SE)

( * ) Notice: Subject to any disclaimer, the term of this patent is extended or adjusted under 35 U.S.C. 154(b) by 18 days.

(21) Appl. No.: 13/141,385

(22) PCT Filed: Dec. 22, 2008

(86) PCT No.: PCT/SE2008/000742
§ 371 (c)(1),
(2), (4) Date: Jun. 22, 2011

(87) PCT Pub. No.: WO2010/074611
PCT Pub. Date: Jul. 1, 2010

(65) Prior Publication Data
US 2011/0257697 A1    Oct. 20, 2011

(51) Int. Cl.
*A61N 1/365* (2006.01)
(52) U.S. Cl.
USPC .............................................. 607/9; 600/547
(58) Field of Classification Search
USPC ................. 600/481, 483, 508–509, 547, 515, 600/526; 607/8–9, 28
See application file for complete search history.

(56) References Cited

U.S. PATENT DOCUMENTS

| 7,082,329 | B2 | 7/2006 | Järverud |
| 7,190,996 | B2 | 3/2007 | Järverud |
| 7,330,759 | B2 | 2/2008 | Militello |
| 2003/0181952 | A1 | 9/2003 | Järverud et al. |
| 2004/0049238 | A1* | 3/2004 | Jarverud ................ 607/17 |
| 2005/0182447 | A1 | 8/2005 | Schecter |
| 2007/0066905 | A1 | 3/2007 | Zhang |
| 2007/0191901 | A1 | 8/2007 | Schecter |
| 2007/0271119 | A1 | 11/2007 | Boerger et al. |
| 2007/0293770 | A1 | 12/2007 | Bour et al. |
| 2008/0082134 | A1 | 4/2008 | Lang |
| 2008/0234773 | A1 | 9/2008 | Ni et al. |
| 2008/0262361 | A1 | 10/2008 | Gutfinger et al. |

FOREIGN PATENT DOCUMENTS

WO   WO 2010/071488 A1   6/2010

OTHER PUBLICATIONS

Analysis of the O-wave in Acute Right Ventricular Apex Impedance Measurements with a Standard Pacing Lead in Animals, Järverud et al., Medical and Biological Engineering & Computing, vol. 40 (2002) pp. 512-519.

* cited by examiner

*Primary Examiner* — Rex R Holmes

(57) ABSTRACT

In an implantable medical device and a method for monitoring ventricular synchronicity of a heart. In particular, impedance signals are measured and an occurrence of a notch is detected in the impedance signal coincident with a period including a change from rapid to slow filling of a ventricle. The notch is indicated by a first positive slope change in a negative slope in a predetermined time window during a diastolic phase of a cardiac cycle. A degree of synchronicity is determined based on the notch feature, wherein a decreasing notch feature indicates an increased degree of synchronicity in the filling phase of the ventricles.

27 Claims, 6 Drawing Sheets

IMPLANTABLE MEDICAL DEVICE AND METHOD FOR MONITORING SYNCHRONICITY OF THE VENTRICLES OF A HEART

BACKGROUND OF THE INVENTION

1. Field of the Invention

The present invention generally relates to the field of implantable heart stimulation devices, such as pacemakers, and similar cardiac stimulation devices that also are capable of monitoring and detecting electrical activities and events within the heart. More specifically, the present invention relates to an implantable medical device and a method for monitoring ventricular synchronicity of a heart.

2. Description of the Prior Art

Implantable heart stimulators that provide stimulation pulses to selected locations in the heart e.g. selected chambers have been developed for the treatment of cardiac diseases and dysfunctions. Heart stimulators have also been developed that affect the manner and degree to which the heart chambers contract during a cardiac cycle in order to promote the efficient pumping of blood.

Furthermore, the heart will pump more effectively when a coordinated contraction of both atria and ventricles can be provided. In a healthy heart, the coordinated contraction is provided through conduction pathways in both the atria and the ventricles that enable a very rapid conduction of electrical signals to contractile tissue throughout the myocardium to effectuate the atrial and ventricular contractions. If these conduction pathways do not function properly, a slight or severe delay in the propagation of electrical pulses may arise, causing asynchronous contraction of the ventricles which would greatly diminish the pumping efficiency of the heart. Patients, who exhibit pathology of these conduction pathways, such as patients with bundle branch blocks, etc., can thus suffer from compromised pumping performance. For example, asynchronous movements of the valve planes of the right and left side of the heart, e.g. an asynchronous opening and/or closure of the aortic and pulmonary valves, is such an asynchrony that affects the pumping performance in a negative way. This may be caused by right bundle branch block (RBBB), left bundle branch block (LBBB), or A-V block. In a well functioning heart, the left and right side of the heart contract more or less simultaneously starting with the contraction of the atria flushing down the blood through the valves separating the atria from the ventricles, in the right side of the heart through the tricuspid valve and in the left side of the heart through the mitral valve. Shortly after the atrial contraction the ventricles contract, which results in an increasing blood pressure inside the ventricles that first closes the A-V plane valves and after that forces the outflow valves to open. In the right side of the heart it is the pulmonary valves that separate the right ventricle from the pulmonary artery that leads the blood to the lung, which is opened. In the left side of the heart the aortic valve separates the left ventricle from the aorta that transports blood to the whole body. The outflow valves, the pulmonary valve and aortic valve, open when the pressure inside the ventricle exceeds the pressure in the pulmonary artery and aorta, respectively. The ventricles are separated by the intraventricular elastic septum. Hence, for a well functioning heart a substantially synchronous operation of the left and right hand side of the heart, e.g. a synchronous opening and/or closure of the aortic and pulmonary, is of a high importance.

When functioning properly, the heart maintains its own intrinsic rhythm. However, patients suffering from cardiac arrhythmias, i.e. irregular cardiac rhythms, and/or from poor spatial coordination of heart contractions often need assistance in form of a cardiac function management system to improve the rhythm and/or spatial coordination of the heart contractions. Such systems are often implanted in the patient and deliver therapy to the heart, such as electrical stimulation pulses that evoke or coordinate heart chamber contractions. Thus, implantable heart stimulators that provide stimulation pulses to selected locations in the heart e.g. selected chambers have been developed for the treatment of cardiac diseases and dysfunctions. Heart stimulators have also been developed that affect the manner and degree to which the heart chambers contract during a cardiac cycle in order to promote the efficient pumping of blood.

In particular, various prior art procedures have been developed for addressing disorders related to asynchronous function of the heart. For instance, cardiac resynchronization therapy (CRT) can be used for effectuating synchronous atrial and/or ventricular contractions. Furthermore, cardiac stimulators may be provided that deliver stimulation pulses at several locations in the heart simultaneously, such as biventricular stimulators. For example, patients with heart failure symptoms and dyssynchronized cardiac chambers are often offered such a CRT device that synchronizes the right and left ventricle to obtain an improved cardiac functional performance and quality of life. The CRT settings should be optimized in terms of VV interval and AV interval for optimized pumping performance. In the majority of CRT patients this optimizing of CRT parameters is normally performed at implant and perhaps at one regular follow-up. Ideally, this optimization should be performed more frequently to match the actual need of the patient.

In a healthy heart the sinus node, situated in the right atrium, generates electrical signals which propagates throughout the heart and control its mechanical movement. Some medical conditions, however, affect the relationship between the electrical and mechanical activity of the heart and, therefore, measurements of the electrical activity only cannot be relied upon as indicative of the true status of the heart or as suitable for triggering stimulation of the heart.

Hence, asynchronous depolarization of the ventricles results in asynchronous myocardial contractions with regional dyskinetic cardiac tissue. The cardiac performance is very sensitive to small asynchronous cardiac movements, as the overall heart cycle is disturbed. One consequence is that not only is the systolic part of the heart cycle is less effective, but the diastolic phase (the filling phase) of the heart cycle may also be greatly tampered.

Consequently, there is a need within the art of methods and devices for obtaining accurate and reliable signals reflecting different aspects of mechanical functioning of the heart, and, in particular, reflecting the synchronicity or dyssynchronicity of the functioning of the ventricles. Impedance measurements, e.g. of the intracardiac impedance, has been shown to provide reliable information regarding the mechanical functioning of the heart. For example, through the impedance measurements, blood volume changes are detectable. Blood has a higher conductivity (lower impedance) than myocardial tissue and lungs. The relationship between the impedance-volume is inverse, the more blood—the smaller impedance. For example, at maximum ventricular filling after atrial contraction, in end-diastole just prior to ventricle contraction, the intracardiac impedance attaints its minimum amplitude during the course of the cardiac cycle.

One phenomenon or characteristic feature that has been observed in the diastolic intracardiac impedance is the so called notch, or intracardiac notch. This feature manifests as a consistent change in the diastolic intracardiac ventricular impedance slope after rapid ventricular filling at the change to slow filling. It has been shown that this feature can be used for diagnostic purposes, see "Studies of changes in volume in right ventricle with electrical bio-impedance", K. Järverud, Licentiate Thesis, Karolinska Institutet, Stockholm, 2002. The notch is defined as the first positive slope on the negative diastolic impedance slope between end of T-wave and P-wave. However, a slope change immediately at the end of T-wave is not considered to be a notch In the prior art, the diastolic notch has been used for diagnostic purposes. For example, in U.S. Pat. No. 7,082,329, the occurrence of the notch in the impedance signal coincident with the entry of blood into the ventricles is monitored to detect signs of disturbed relaxation patterns of the heart. The time derivative of the intra-cardiac impedance signal is calculated and a loop is generated by the calculated time derivative values for each cardiac cycle. The generated loop is compared with a loop template representing a normal loop for the patient to identify deviations in the loop from normal deviations in timing and shape of the loop. Furthermore, in U.S. Pat. No. 7,190,996, the notch is used for early detection of ischemic heart disease. The occurrence of the notch in the impedance signal coincident with the entry of blood into the ventricles is monitored and a measured post-notch impedance curve is compared with a stored predetermined reference impedance curve template to detect an ischemic heart disease from the result of the comparison. Thus, the intracardiac impedance and characteristic features of the impedance have been used within the art for different diagnostic purposes. Even though the intra-cardiac impedance notch has been used to monitor and detect certain cardiac deficiencies such ischemic heart disease, there remains a need for an efficient and accurate parameter for monitoring and detecting disturbances in the filling pattern of the ventricles and the synchronicity in the functioning of the ventricles. On the other hand, the intracardiac impedance signal has been used within the art to monitor the synchronicity of the ventricles and to optimize the functioning of the ventricles. For, example, in US 2007/0066905, a system for optimizing a cardiac synchronization based on measured impedance signals is shown. In one embodiment of the system, the left ventricular impedance is measured, which reflects the contraction and expansion of the left ventricle. The obtained impedance signals are used to compute the impedance-indicated peak-to-peak volume indication of the left ventricle and/or an impedance-indicated maximum rate of change in the left ventricular volume. These parameters are then used to control a cardiac resynchronization. In US 2007/0271119 a similar optimization system is described. In U.S. Pat. No. 7,330,759, a cardiac pacemaker for bi-ventricular stimulation where impedance signals is used to obtain a synchronization of the left and right ventricles is shown. In particular, the second derivative of the intracardiac impedance pattern of a cardiac cycle is determined and maximized. This is based on the assumption that the intracardiac impedance pattern respectively reflects the volume of blood in a heart, the maximum acceleration to which the blood is subjected to in the heart is to be gauged from the maximum of the second derivative of that intracardiac impedance pattern, which value is correlated to contractility of the left ventricle. These parameters of the impedance signal used for the optimization is dependent on the physiological system including, inter alia, the heart and the vascular system which, for example, may entail that a response to a change of the stimulation parameters in terms of a change of a monitored parameter will be able to detect with a delay. This may, for example, lead to an overcompensation of the stimulation parameters. Furthermore, it cannot be ascertained that the monitored parameters reflect only the hemodynamical performance of the heart, which, in turn, may lead to a stimulation parameter setting that in the long-term is not optimal with respect to the hemodynamic performance of the heart.

In summary, the prior art presents a number of approaches to monitor and detect different cardiac deficiencies based on intracardiac impedance and certain morphology features of the intracardiac impedance. However, there is still a need of a reliable parameter that provides accurate and reliable information of the mechanical functioning of the heart that can be used to monitor and detect a dyssychronism in the functioning of the ventricles during the filling phase. Moreover, in order to be able to optimize the functioning of the heart it is also of paramount interest to obtain information that may enable a fast and reliable optimization of the hemodynamic performance of the heart and, in particular, a fast and reliable synchronization of the ventricles to obtain a coordinated filling phase of the ventricles.

SUMMARY OF THE INVENTION

An object of the present invention is to provide an improved device and method for obtaining impedance information that, in accurate and reliable manner, reflects the mechanical functioning of the heart in order to monitor and detect a dyssychronism in the functioning of the ventricles during the change from the rapid filling phase to the slow filling phase.

The present invention is based on the finding that the intra-cardiac impedance notch is influenced by the synchronicity of the functioning of the ventricles in that the notch becomes a more dominant feature in case of exaggerated dyssynchronicity. The notch is defined as the first positive slope on the negative diastolic impedance slope between end of T-wave and P-wave and there is a close link between the notch and myocardial movements in the change from the rapid filling phase of diastole to the slow filling phase of diastole. The notch is caused by a ventricular wall movement generated by the change from rapid blood inflow to slow blood inflow associated with diastole going from rapid filling to slow filling. In systole, continuous venous return of blood back to the heart is constantly ongoing causing a slight increase in superior vena cava and inferior vena cava pressure. The surplus of venous pressure causes a trajectory of blood in early diastole directly after atrioventricular valves open. As the atrioventricular valve opens and ventricular filling starts, the right and left ventricle are filled rapidly as venous return of blood is ejected into the ventricular cavities. The early filling of blood in the ventricle causes a blood swirl flow in which the blood is flowing or rotating. However, slightly before the swirl blood flow pattern in the early stage of diastole, the blood stream into the ventricle hits the ventricular wall causing it to vibrate, bulge or move. This movement or vibration or level of bulging depends on myocardial wall status or level of disease. In a healthy heart, the right and left heart work synchronously and, hence, the early diastolic movement, bulging, or vibration occurs simultaneously. However, when the right and left ventricle are asynchronous as in the case of heart failure or in bundle branch block, systole and diastole are not synchronous. Rapid filling onset occurs at slightly different time points and therefore, the ventricular wall movement, bulging, or vibration caused by rapid filling will occur at slightly different points of time in the heart cycle. Also, if the left heart wall is in a different state compared to normal, this will influence the movement, bulging or vibration of the left ventricular wall during left side diastole. The present invention is based on this insight and utilizes intra-cardiac impedance to measure these wall vibrations. These wall vibrations are transported through the myocardial wall, and can thus be detected from the right ventricle. In the case of a synchronous heart, the right heart diastolic notch and left heart diastolic notch coincide. In the case of an asynchronous heart, the left and right diastolic notch does not coincide and the notch will be more salient. Thus, by adjusting pacing parameters, e.g. adjusting the VV interval, to minimize the notch, appropriate left-right timing can be achieved.

According to a first aspect of the present invention, there is provided an implantable medical device for monitoring ventricular synchrony of a heart of patient including a pace pulse generator adapted to produce cardiac stimulating pacing pulses and being connectable to at least one medical lead for delivering bi-ventricular pulses to cardiac tissue of the heart. The implantable medical device comprises an impedance measuring unit adapted to, during impedance measuring sessions, measure impedance signals using an electrode configuration, the configuration being connectable to the impedance measuring unit and interacting with the patient, a notch detecting unit adapted to detect an occurrence of a notch in the impedance signal coincident with a period including a change from rapid to slow filling of a ventricle, the notch being indicated by a first positive slope change in a negative slope in a predetermined time window during a diastolic phase of a cardiac cycle, wherein a portion of the impedance signal within a time window surrounding the notch being a notch impedance curve, a notch feature determining unit adapted to determine notch feature using the notch impedance curve, and a synchronicity determining unit adapted to determine a degree of synchronicity based on the notch feature, wherein a decreasing notch feature indicates an increased degree of synchronicity in the filling phase of the ventricles.

According to a second aspect of the present invention, there is provided a method for monitoring ventricular synchrony of a heart of patient in an implantable medical device including a pace pulse generator adapted to produce cardiac stimulating pacing pulses and being connectable to at least one medical lead for delivering bi-ventricular pulses to cardiac tissue of the heart. The method comprises, during impedance measuring sessions, measuring impedance signals using an electrode configuration being connectable to the impedance measuring unit and interacting with the patient, detecting an occurrence of a notch in the impedance signal coincident with a period including a change from rapid to slow filling of a ventricle, the notch being indicated by a first positive slope change in a negative slope in a predetermined time window during a diastolic phase of a cardiac cycle, wherein a portion of the impedance signal within a time window surrounding the notch being a notch impedance curve, determining notch feature using the notch impedance curve; and determining a degree of synchronicity based on the notch feature, wherein a decreasing notch feature indicates an increased degree of synchronicity in the filling phase of the ventricles.

According to a third aspect of the present invention, there is provided a method for optimizing lead and/or electrode locations, the electrodes being connectable to an implantable medical device comprising a pace pulse generator adapted to produce cardiac stimulating pacing pulses and being connectable to at least one medical lead for delivering stimulation pulses to cardiac tissue of the heart. The method includes:

a) measuring impedance signals at a first electrode configuration, wherein the electrodes of the electrode configuration are connectable to the implantable medical device and are located at a right side of the heart;

b) detecting an occurrence of a notch in the impedance signal coincident with a period including a change from rapid to slow filling of a ventricle, the notch being indicated by a first positive slope change in a negative slope in a predetermined time window during a diastolic phase of a cardiac cycle, wherein a portion of the impedance signal within a time window surrounding the notch being a notch impedance curve;

c) determining notch feature using the notch impedance curve for the electrode configuration;

d) determining a degree of synchronicity based on the notch feature for the electrode configuration, wherein a decreasing notch feature indicates an increased degree of synchronicity in the filling phase of the ventricles e) performing an optimization procedure based on the notch feature by iteratively adjust a VV-interval so as to minimize the notch feature in the predetermined time window for the first electrode configuration;

f) repeating (a)-(e) for at least a second electrode configuration;

g) comparing the minimum notch feature for each configuration to identify a overall minimum notch feature; and h) selecting the electrode configuration being associated with the minimum notch feature.

According to a fourth aspect of the present invention, there is provided a system for optimizing lead and/or electrode locations including an implantable medical device, the device including a pace pulse generator adapted to produce cardiac stimulating pacing pulses and being connectable to at least one medical lead for delivering stimulation pulses to cardiac tissue of the heart; an impedance measuring unit adapted to, during impedance measuring sessions, measure impedance signals obtained at a first electrode configuration the configuration being connectable to the impedance measuring unit and interacting with the patient, a notch detecting unit adapted to detect an occurrence of a notch in the impedance signal coincident with a period including a change from rapid to slow filling of a ventricle, the notch being indicated by a first positive slope change in a negative slope in a predetermined time window during a diastolic phase of a cardiac cycle, wherein a portion of the impedance signal within a time window surrounding the notch being a notch impedance curve, a notch feature determining unit adapted to determine notch feature using the notch impedance curve; and a synchronicity determining unit adapted to determine a degree of synchronicity based on the notch feature, wherein a decreasing notch feature indicates an increased degree of synchronicity in the filling phase of the ventricles; and an external control unit connectable to the implantable medical device and being adapted to instruct the implantable medical device to obtain a notch feature for at least a second electrode configuration, to compare the minimum notch feature for each configuration to identify a overall minimum notch feature, and to select to the electrode configuration being associated with the minimum notch feature.

According to yet another aspect of the present invention, there is provided a pacing analyzer for optimizing lead and/or electrode locations being connectable to at least one medical lead implantable in a heart of a patient. The analyzer includes a pace pulse generator adapted to produce cardiac stimulating pacing pulses and being connectable to at least one medical lead for delivering stimulation pulses to cardiac tissue of the heart; an impedance measuring unit adapted to, during impedance measuring sessions, measure impedance signals obtained at an electrode the configuration being connectable to the impedance measuring unit and interacting with the patient, a notch detecting unit adapted to detect an occurrence of a notch in the impedance signal coincident with a period including a change from rapid to slow filling of a ventricle, the notch being indicated by a first positive slope change in a negative slope in a predetermined time window during a diastolic phase of a cardiac cycle, wherein a portion of the impedance signal within a time window surrounding the notch being a notch impedance curve, a notch feature determining unit adapted to determine notch feature using the notch impedance curve; a synchronicity determining unit adapted to determine a degree of synchronicity based on the notch feature, wherein a decreasing notch feature indicates an increased degree of synchronicity in the filling phase of the ventricles, a VV delay determining unit adapted to perform an optimization procedure, wherein the pace pulse generator is controlled to, based on the notch feature, iteratively adjust a VV-interval so as to minimize the notch feature in the predetermined time window; and a control unit adapted to: compare the minimum notch feature for different electrode and/or lead configurations to identify a overall minimum notch feature, and indicate the electrode configuration being associated with the minimum notch feature.

According to an embodiment of the present invention, a notch is detected as the first positive slope change in a negative slope in a predetermined time window during a diastolic phase of a cardiac cycle, wherein the predetermined time window starts a predetermined period of time from the end of the systolic phase.

In an embodiment of the present invention, a first derivative of the measured impedance signal is calculated, which notch is indicated by a first positive slope change after a zero derivative of the impedance signal. The inventor has discovered that the time derivative provides accurate information of the notch and accurate and reliable information for determination of the notch feature.

According to an embodiment of the present invention, the notch feature is based on a notch start point. The notch start point is measured from the first point of a zero derivative of the impedance signal after the T-wave, wherein a longer period between the first point of a zero derivative and the notch indicates a higher degree of dyssynchronicity. At dyssynchronicity, the occurrence of the notch is delayed in relation to the T-wave, or at a later point in relation to the maximum of the impedance signal (i.e. at the first zero point of the time derivative of the impedance signal after the T-wave), in comparison to the synchronous case.

In another embodiment of the present invention, the notch feature is based on a notch width, which notch width is determined to be a distance from the notch to the first point of a zero derivative after the notch, wherein a wider notch width indicates a higher degree of dyssynchronicity. In an asynchronous case, the notch width measured, for example, along a threshold relative to a maximum of the time derivative will increase.

Further, in yet another embodiment of the present invention, the notch feature is based on the notch area. The notch area is determined to be an area of the differentiated notch impedance curve between the notch and the first point of a zero derivative after the notch or between two intersection points of the differentiated notch impedance curve and a threshold relative to the maximum of the derivate of the notch impedance curve, wherein a larger notch area indicates a higher degree of dyssynchronicity. To determine the area, the differentiated signal curve between the notch and the first point of a zero derivative after the notch or between two intersection points of the differentiated notch impedance curve and a threshold relative to the maximum of the derivate of the notch impedance curve can be integrated.

According to one embodiment of the present invention, the notch feature is used in an optimization procedure and a VV interval or delay is optimized, based on the notch feature, by iteratively adjusting the VV-interval and/or the AV-interval so as to minimize the notch feature.

Thereby, the advantage of a fast and reliable optimization of the hemodynamic performance of the heart and, in particular, a fast and reliable synchronization of the ventricles, i.e. a coordinated contraction of the ventricles, may be achieved. A further advantage that may be obtained is a, in the long-term, optimal synchronization of the ventricles, i.e. a coordinated contraction of the ventricles, which will improve the hemodynamic performance of the heart.

According to an embodiment of the present invention, a breath rate sensor is adapted to sense a breathing cycle of the patient, wherein the notch feature can be determined in synchronism with an event of a breathing cycle or respiration cycle of the patient or as an average value over a predetermined number of breathing cycles. Thereby, the accuracy of the determination of the notch feature can be significantly improved. This is due to the fact that the cardiogenic impedance is greatly affected by the respiration. Therefore, by synchronizing the determination of the notch feature with a particular event in the respiration cycle or by determining the feature as an average value over a number of respiration cycles, the influence of the respiration on the impedance causing variability in the impedance signal can be eliminated or at least significantly reduced.

In a further embodiment of the present invention, a body posture sensor is adapted to sense a body posture of the patient, wherein the notch feature can be determined in synchronism with a predetermined body posture of the patient, or as an average value of the notch feature of at least two body postures. Thereby, the accuracy in the determination of the notch feature can be significantly improved. This is due to the fact that the cardiogenic impedance is greatly affected by the body posture of the patient. Therefore, by synchronizing the determination of the notch feature with a particular body posture or by determining the feature as an average value over a more than one body posture, the influence of the body posture on the impedance causing variability in the impedance signal can be eliminated or at least significantly reduced.

Further embodiments include an activity sensor adapted to sense an activity level of the patient and a heart rate sensor adapted to sense a heart rate of the patient, respectively, and the notch feature may thus be determined in synchronism with a predetermined activity level of the patient or in synchronism with a predetermined heart rate or heart rate interval of the patient.

According to embodiments, one or several of the sensors including a heart rate sensor, a breath rate sensor, an activity sensor, and/or body posture sensor may be combined.

According to an embodiment, a matrix of notch features can be determined. For example, different features for different body postures and for different activity levels may be included in the matrix. Further, different notch features may be determined for different events in the respiration cycle and for systole and diastole. During an optimization, the notch feature corresponding to the present conditions of the patient can be selected and optimized.

In an embodiment of the present invention, IEGM signals of consecutive cardiac cycles are sensed and cardiac events are detected in the cardiac cycles using the IEGM signals. A time window is determined based on the detected cardiac events and the IEGM signals and/or impedance signals. For example, a time window including a diastolic phase of the cardiac cycle can be determined to extend between a period starting at a detection of a T-wave and ending at a detection of an R-wave.

As the skilled person realizes, steps of the methods according to the present invention, as well as preferred embodiments thereof, are suitable to realize as computer program or as a computer readable medium.

Further objects and advantages of the present invention will be discussed below by means of exemplifying embodiments.

DESCRIPTION OF THE PREFERRED EMBODIMENTS

The following is a description of exemplifying embodiments in accordance with the present invention. This description is not to be taken in limiting sense, but is made merely for the purposes of describing the general principles of the invention. Thus, even though particular types of implantable medical devices such as heart stimulators will be described, e.g. biventricular pacemakers, the invention is also applicable to other types of cardiac stimulators such as dual chamber stimulators, implantable cardioverter defibrillators (ICDs), etc.

Figure 1A:
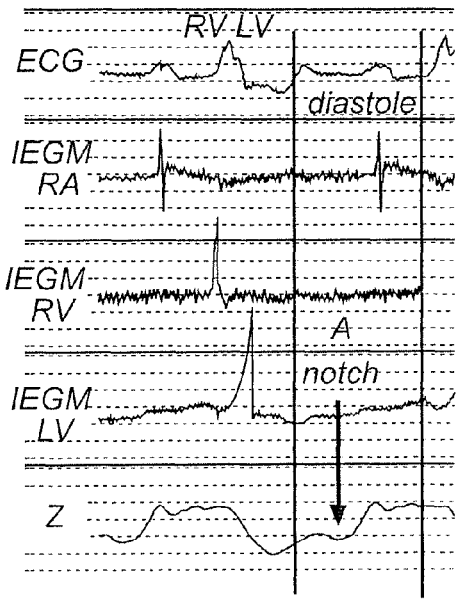
FIG. 1a-1c show measurements performed on a patient at intrinsic rhythm, RV/LV synchronized, and RV paced before LV, respectively.
Figure 1B:
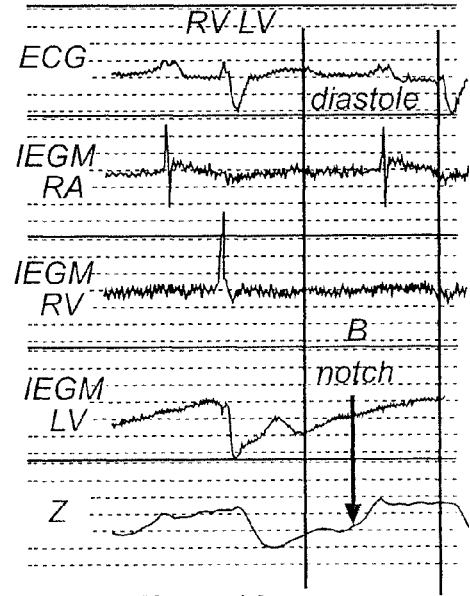
Figure 1C:
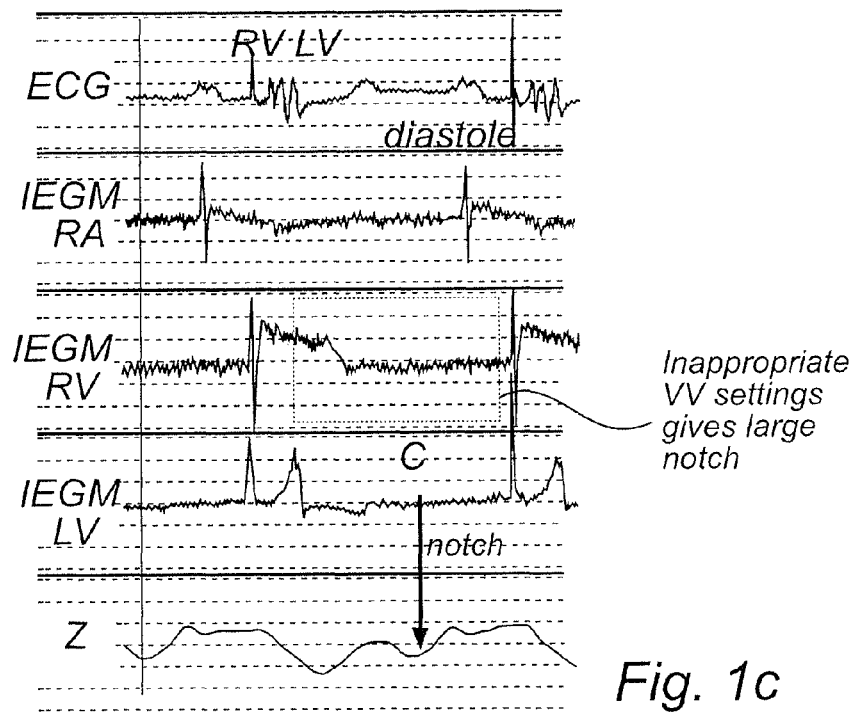

Asynchronous depolarization of the ventricles results in asynchronous myocardial contractions with dyskinetic cardiac tissue. The cardiac performance is very sensitive to small asynchronous cardiac movements, as the overall heart cycle is disturbed. One consequence is that not only the systolic part of the heart cycle is less effective, the diastolic part (filling phase) of the heart cycle may also be disturbed. This can be observed by monitoring the diastolic notch since the cardiogenic impedance changes considerably during diastole, especially around the diastolic notch at such disturbances. The notch becomes a more dominant feature at asynchronous depolarization. In FIGS. 1a-1c it is shown that the notch becomes a more dominant feature in case of exaggerated dyssynchronized pacing with RV paced before LV in a patient with LBBB ("Left Bundle Brach Block"). In FIG. 1a, data from a patient at an intrinsic rhythm is shown, in FIG. 1b data from the same patient at synchronized RV and LV pacing, and in FIG. 1b data from the same patient but at RV paced before LV. As can be seen, the notch, indicated with the arrows A, B, and C, respectively, is more dominant in FIG. 1c, i.e. at RV paced before LV, compared with the notch in FIGS. 1a and 1b.

Figure 2:
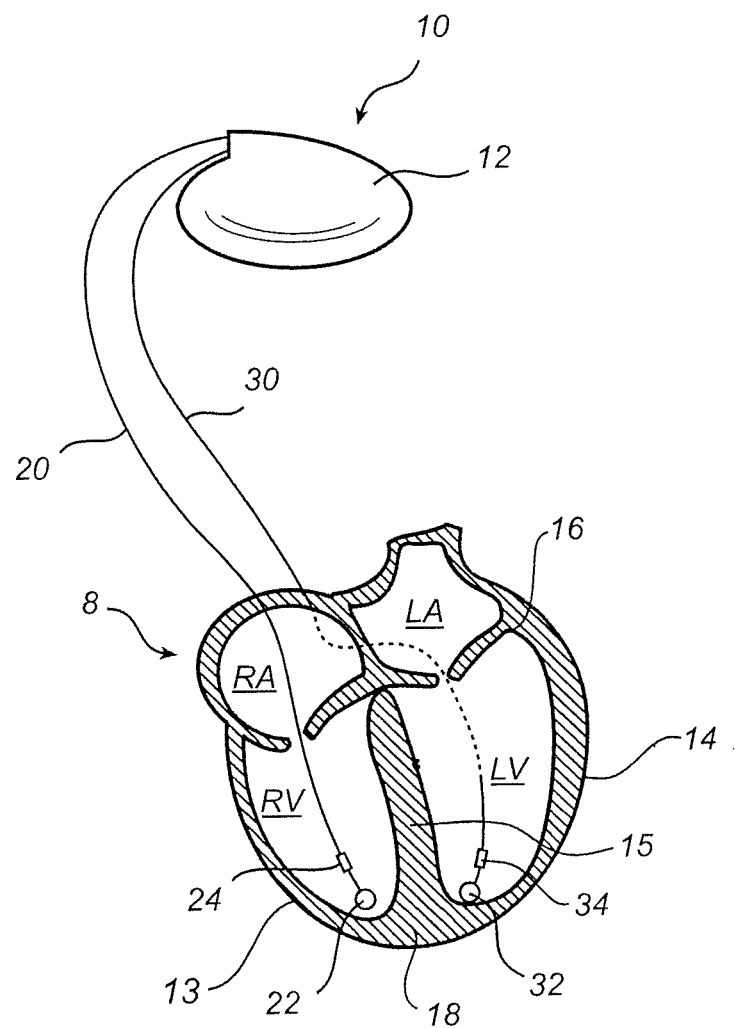
FIG. 2 schematically illustrates an implantable medical device according to an embodiment of the present invention.

Referring now to FIG. 2, there is shown an implantable medical device according to an embodiment of the present invention. According to this embodiment, the invention is implemented in a stimulation device 10. The stimulation device 10 is in electrical communication with a patient's heart 8 by way of medical leads 20 and 30 suitable for delivering multi-chamber stimulation, which leads 20 and 30 are connectable to the stimulator 10. The illustrated portions of the heart 8 include right atrium RA, the right ventricle RV, the left atrium LA, the left ventricle LV, right ventricular wall 13, left ventricular wall 14, the ventricle septum 15, the valve plane 16, and the apex 18.

In order to sense right ventricular and atrial cardiac signals and impedances and to provide stimulation therapy to the right ventricle RV, the implantable medical device 10 is coupled to an implantable right ventricular lead 20, which may have a ventricular tip electrode 22 and a ventricular annular or ring electrode 24. The right ventricular tip electrode 22 is in this embodiment arranged to be implanted in the endocardium of the right ventricle, e.g. near the apex 18 of the heart 8. Thereby, the tip electrode 22 becomes attached to cardiac wall. In this example, the tip electrode 22 is fixedly mounted in a distal header portion of the lead 20.

Furthermore, in order to sense left atrium and ventricular cardiac signals and impedances and to provide pacing therapy for the left ventricle LV, the implantable medical device 10 is coupled to a "coronary sinus" lead 30 designed for placement via the coronary sinus in veins located distally thereof, so as to place a distal electrode adjacent to the left ventricle and an electrode adjacent to the right atrium RA. The coronary sinus lead 30 is designed to receive ventricular cardiac signals from the cardiac stimulator 10 and to deliver left ventricular LV pacing therapy using at least a left ventricular tip electrode 32 to the heart 8. In the illustrated example, the LV lead 30 further comprises an annular ring electrode 34 for sensing electrical activity related to the left ventricle LV of the heart 8. A right atrium lead (not shown) may also be included, which may be designed to receive right atrium cardiac signals from the cardiac stimulator 10 and to deliver right atrium RA pacing therapy using for example right atrium ring electrode.

With reference to the configuration shown in FIG. 2, a number of impedances vectors that can be used for obtaining impedance data that reflect left ventricular wall and right ventricular wall movements, bulging, or vibrations in left side diastole and the right side diastole will be described. At synchronous work of left and right ventricle, the early diastolic movement, bulging or vibration occur simultaneously. However, at asynchronous work of the right and left ventricle, as in case of heart failure or bundle branch block, the systolic phase and the diastolic phase will also be asynchronous. Rapid filling onset will thus occur at slightly different points of time in the cardiac cycle and therefore the ventricular wall movement, bulging or vibration caused by the rapid filling will occur at different points of time. For example, an impedance measurement wherein the current is applied between the ring electrode 24 of the right ventricle and the tip electrode 22 of the right ventricle, and the resulting impedance is measured between the same electrodes. A further alternative is an impedance measurement vector where the current is applied between the ring electrode 24 of the right ventricle and the case 12. The resulting impedance is measured between the same electrodes. As the skilled person realizes, there are a number of other conceivable measurement vectors that can be used to measure impedance reflecting the right ventricular wall 13 and left ventricular wall 14 movements, for example, between right ventricle electrodes 22 and/or 24 and left ventricle electrodes 32 and/or 34.

Figure 3:
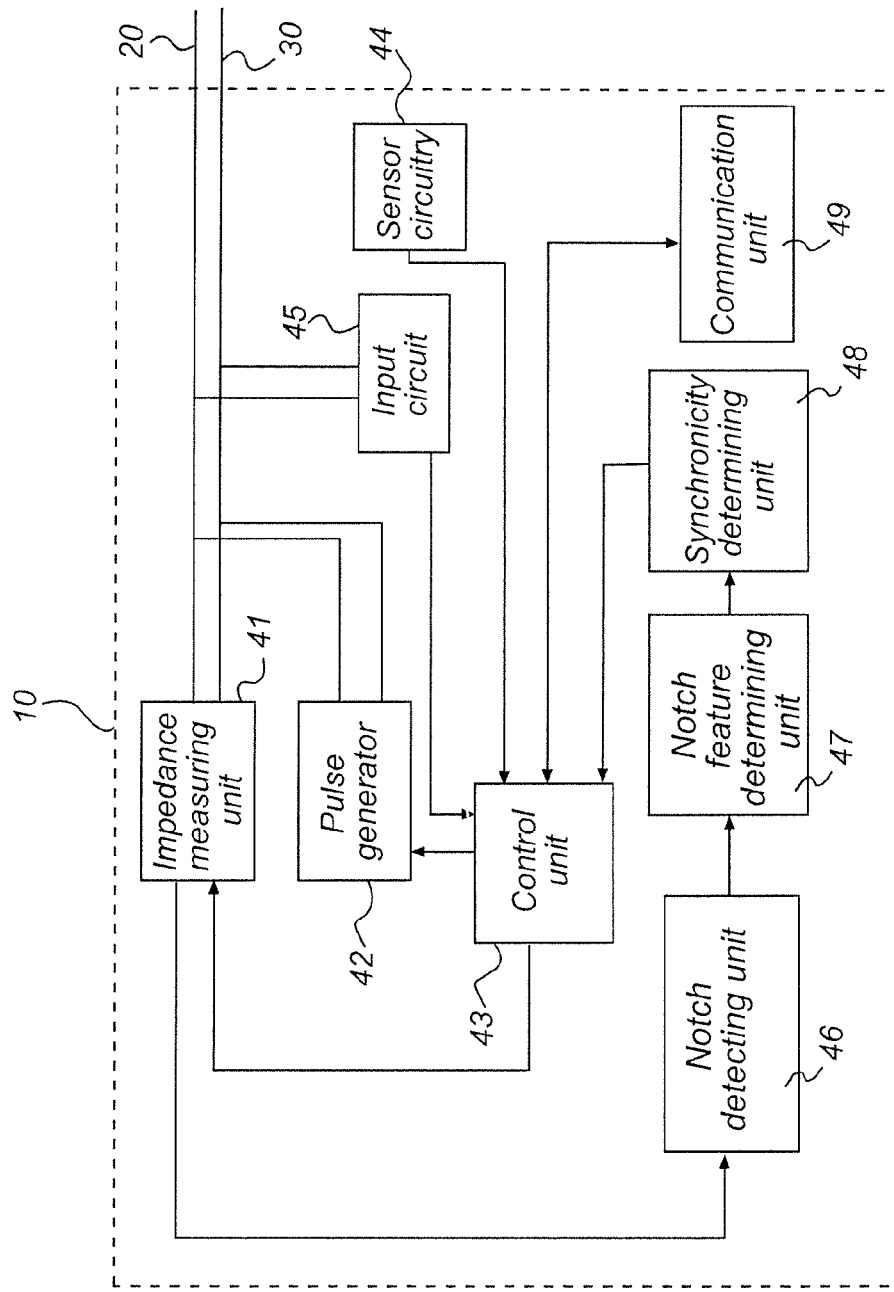
FIG. 3 is schematic block diagram showing the implantable medical device of FIG. 3 in more detail.
Figure 4:
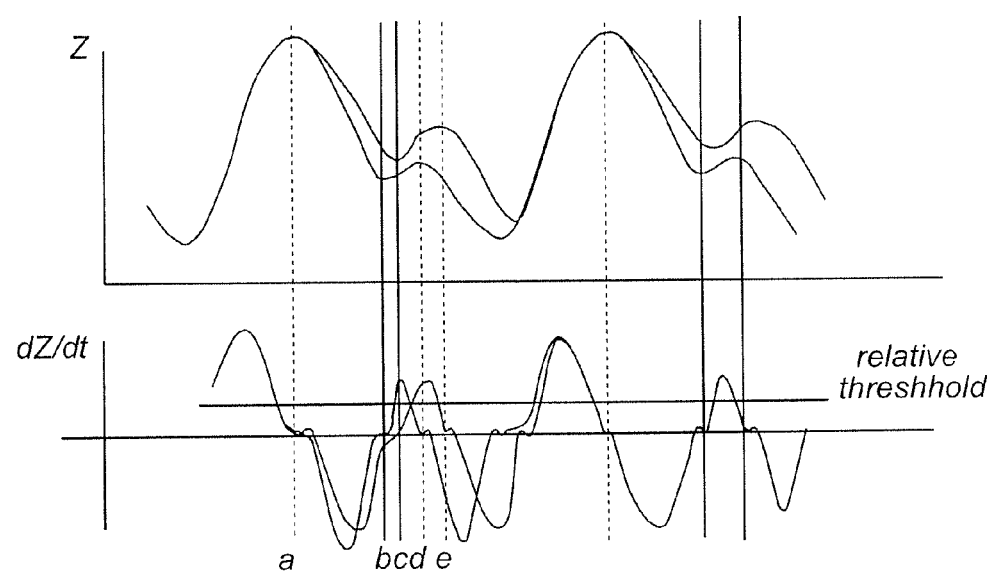
FIG. 4 schematically shows impact on the impedance signal and on the differentiated impedance signal resulting from asynchronous contractions.

Turning now to FIG. 3, the heart stimulator 10 of FIG. 4 is shown in a block diagram form. For illustrative purposes, reference is made to FIG. 2 for the elements of the leads that are intended for positioning in or at the heart.

An embodiment of the implantable medical device according to the present invention will be shown. The heart stimulator 10 comprises a housing 12 being hermetically sealed and biologically inert, see FIG. 2. Normally, the housing is conductive and may, thus, serve as an electrode. One or more pacemaker leads, where only two are shown in FIGS. 2, 20 and 30, are electrically coupled to the implantable medical device 10 in a conventional manner. The leads 20, 30 extend into the heart (see FIG. 2) via a vein of the patient.

As discussed above with reference to FIG. 2, the leads 20, 30 comprises one or more electrodes, such a tip electrodes or a ring electrodes, arranged to, inter alia, transmit pacing pulses for causing depolarization of cardiac tissue adjacent to the electrode (-s) generated by a pace pulse generator 42 under influence of a control circuit 43 comprising a microprocessor and for measuring impedances. The control circuit 43 controls, inter alia, pace pulse parameters such as output voltage and pulse duration and includes a memory circuit (not shown), which memory circuit may include a random access memory (RAM) and/or a non-volatile memory such as a read-only memory (ROM). Detected signals from the patient's heart are processed in an input circuit 45 and are forwarded to the microprocessor of the control circuit 43 for use in logic timing determination in known manner.

Furthermore, an impedance measuring unit 41 is adapted to carry out impedance measurements of the cardiac impedance of the patient indicative of ventricular wall movements, vibrations or bulgings. This can be achieved by means of a measurement vector in which the ring electrode 24 and the tip electrode 22 of the right ventricle is used both for applying a voltage and for measuring the resulting current. A further alternative is an impedance measurement vector where the current is applied between the ring electrode 24 of the right ventricle and the tip electrode 32 of the left ventricle. The resulting impedance can be measured between the same electrodes. The impedance measuring unit 41 may comprise an amplifier (not shown) that amplifies the evoked voltage response, i.e. the measured voltage, and may be synchronized with the excitation current. Thus, the impedance measuring unit 41 obtains the cardiac impedance given by the delivered current and the evoked voltage response. The impedance measuring unit 41 may also comprise a filtering circuit (not shown), for example, a Gaussian filter.

Furthermore, a notch detecting unit 46 adapted to detect an occurrence of a notch in the impedance signal coincident with a filling phase of a ventricle, wherein a portion of the impedance signal within a time window surrounding the notch being a notch impedance curve. Hence, the notch detecting unit 46 is adapted to detect the existence of notches from the measured impedance signal and, if so, the timing in the cardiac cycle of the notch. The notch detecting unit 46 is adapted to, as an alternative, the existence of a notch from the time derivative of the impedance signal. In particular, the notch detecting unit 46 is adapted, as will be described in more detail below with reference to FIGS. 4 and 5, to detect a notch as the first positive slope change in a negative slope in a predetermined time window during a diastolic phase of a cardiac cycle, wherein the predetermined time window starts each predetermined period of time from the end of the systolic phase A notch feature determining unit 47 is connected to the notch detecting unit 46 and is adapted to determine notch feature using the notch impedance curve. The notch feature determining unit may also be adapted to calculate a first derivative of the of the measured impedance signal. The notch feature determining unit 47 may include a storage part or memory part for continuous storage, e.g. temporary, of notch shapes in the impedance signal or in the first derivative of the impedance signal, R-wave to notch time correlated to heart rate, notch shape, notch impedance curve, etc.

Moreover, the heart stimulator 10 includes a synchronicity determining unit 48 adapted to determine whether contractions of the heart is synchronous or dyssynchronous based on the notch characteristics.

The heart stimulator 10 also includes sensor circuits 44, for example, a respiration sensor for sensing a respiration rate or breathing rate and/or a body posture sensor for sensing a body posture of the patient. Additional sensors may include a heart rate sensor and/or an activity level sensor. The sensor circuit may be arranged in a medical lead 20, 30 or within the heart stimulator 10.

Turning now to FIG. 4, the impact on the impedance morphology resulting from asynchronous filling will be discussed. As discussed above, the notch is caused by a ventricular wall movement generated by the change from rapid blood inflow to slow blood inflow associated with diastole and a dyssynchronicity in the work of left and right ventricular will result in a dyssynchronicity in the onset of rapid filling. Thus, in the case of asynchronous heart, the left and right diastolic notch will not coincide, and, therefore, the notch will be enlarged under such conditions. In FIG. 4, the upper diagram schematically displays impedance signals measured in a synchronous heart and in an asynchronous heart, respectively. The impedance signal 50 is measured during synchronous work by the ventricles and the impedance signal and the impedance signal 51 is measured during asynchronous work by the ventricles. In the lower diagram, the first derivative 52 and 53, respectively, of the impedance signals for the synchronous case and the asynchronous case, respectively, shown in the upper diagram are schematically illustrated. The notch is defined as the first positive slope change, i.e. indicated with (b) in FIG. 4, after the T-wave and after zero first derivative of the impedance (a). Under normal conditions, i.e. at synchronous work, the notch width is (b)-(d), i.e. the distance between the notch and the first zero derivative of the impedance signal after the notch. In the asynchronous case, the notch occurs at a later point in time (c) relative to the maximum impedance and its width is enlarged (c)-(e). Further, the area of the curve corresponding to the differentiated impedance between the notch and the first zero derivative of the impedance signal after the notch is enlarged during asynchronous work.

According to an embodiment of the present invention, the notch feature is based on a notch start point, the notch start point being measured from the first point of a zero derivative of the impedance signal after the T-wave, wherein a longer period between the first point of a zero derivative and the notch indicates a higher degree of dyssynchronicity. With reference to FIG. 4, the notch start point may be defined as the period of time between the maximum impedance (a) and the point in time when the notch is detected. That is, in FIG. 4, the period of time between points indicated with (a) and (b), for synchronous work, and between points indicated with (a) and (c) for asynchronous work. In order to obtain a more synchronous work of the ventricles, this period of time can be minimized.

In another embodiment of the present invention, the notch feature is based on a notch width, which notch width is determined to be a distance from the notch to the first point of a zero derivative after the notch, wherein a wider notch width indicates a higher degree of dyssynchronicity. With reference to FIG. 4, the notch width is defined to be the distance between (b)-(d), in the synchronous case, and (c)-(e), in the asynchronous case, respectively. The notch width can be determined by applying a threshold, referred to as relative threshold, relatively to the maximum of the derivative of the impedance, referred to in FIG. 4 as relative threshold. In order to obtain a more synchronous work of the ventricles, the notch width should be minimized.

According to another embodiment of the present invention, the notch feature is based on a notch area. The notch are may be determined to be an area of the differentiated notch impedance curve between the notch and the first point of a zero derivative after the notch or between two intersection points of the differentiated notch impedance curve and a threshold relative to the maximum of the derivate of the notch impedance curve, wherein a larger notch area indicates a higher degree of dyssynchronicity. To calculate the area, the curve part of the differentiated notch impedance curve from the notch to the first point of a zero derivative after the notch or between two intersection points of the differentiated notch impedance curve and a threshold relative to the maximum of the derivate of the notch impedance curve can be integrated.

The notch feature can be a combination of one or more of the above mentioned alternatives, for example, a weighted average value of the of the notch features e.g. notch start point and notch width.

In another embodiment of the present invention, the notch feature is determined to be the shape of the impedance waveform during a time window following the notch. With reference to FIG. 4, the waveform is the part of the impedance signal between (b)-(d) in the synchronous case and the signal between (c)-(e) in the asynchronous case.

Figure 5:
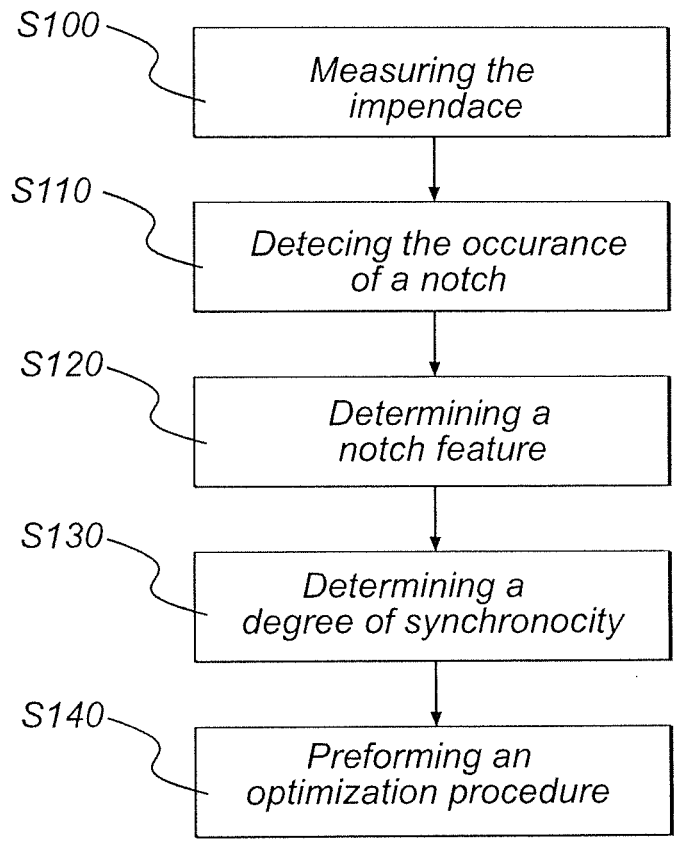
FIG. 5 is a flow chart showing the general principles for a method according to the present invention.

With reference now to FIG. 5, the general concept of the method monitoring ventricular synchrony of a heart according to the present invention will be described. The method may be implemented in an implantable medical device (e.g. a device described above with reference to FIGS. 2 and 3) comprising a pace pulse generator adapted to produce cardiac stimulating pacing pulses and being connectable to at least one medical lead for delivering stimulation pulses to cardiac tissue of the heart. The method includes a first step, S100, of, during impedance measuring sessions, measuring impedance signals by an electrode configuration being located such that the impedance signals substantially reflects movements, bulgings or vibrations during change from the rapid filling phase to the slow filling phase. Then, at step S110, an occurrence or existence of a notch is detected in the impedance signal coincident with a filling phase of a ventricle, which notch is indicated by a first positive slope change in a negative slope in a predetermined time window during a diastolic phase of a cardiac cycle. Further, a portion of the impedance signal within a time window surrounding the notch is defined a notch impedance curve. In an embodiment of the present invention, the notch impedance curve is a curve part following the notch within a predetermined time window, for example, starting at the notch and ending at the onset of the P-wave. The detection of the existence of a notch in a cardiac cycle may be started at end of the T-wave and/or at the first zero derivative of the impedance signal or at a refractory period starting at the end of the T-wave, for example, having a length of about 50-100 msec. Thereafter, at step S120, a notch feature is determined using the notch impedance curve. As have been described above, with reference to FIG. 4, for example, the notch feature may be a notch start point. The notch start point can be measured from the first point of a zero derivative of the impedance signal after the T-wave, wherein a longer period between the first point of a zero derivative and the notch indicates a higher degree of dyssynchronicity. Further, the notch feature may be, and, or alternatively, be a notch width. The notch width can be determined to be a distance from the notch to the first point of a zero derivative after the notch measured along a predetermined threshold relatively to a maximum time derivative of the impedance signal within the notch impedance curve. A wider notch width indicates a higher degree of dyssynchronicity. Moreover, a notch area may, and, or alternatively, be determined by integration to be an area of the differentiated notch impedance curve between the notch and the first point of a zero derivative after the notch or between two intersection points of the differentiated notch impedance curve and a threshold relative to the maximum of the derivate of the notch impedance curve. A larger notch area indicates a higher degree of dyssynchronicity. Furthermore, in another alternative a shape of the notch impedance curve is determined to be the notch feature. At step S130, a degree of synchronicity based on the notch feature is determined. A decreasing notch feature indicates an increased degree of synchronicity in the filling phase of the ventricles. Optionally, at step S140, an optimization procedure is performed, wherein the pace pulse generator 42 is controlled to, based on the notch feature, to iteratively adjust a VV-interval so as to minimize the notch feature so as to obtain substantially synchronized ventricle contractions. In case a curve shape is used as notch feature, an optimization procedure, wherein the pace pulse generator 42 is controlled to, based on the curve shape, iteratively adjust a VV-interval so as to obtain a smooth notch impedance curve. Alternatively, a pattern comparison can be made with a reference impedance curve to obtain comparison result and to determine a degree of synchronicity based on this comparison result.

Figure 6:
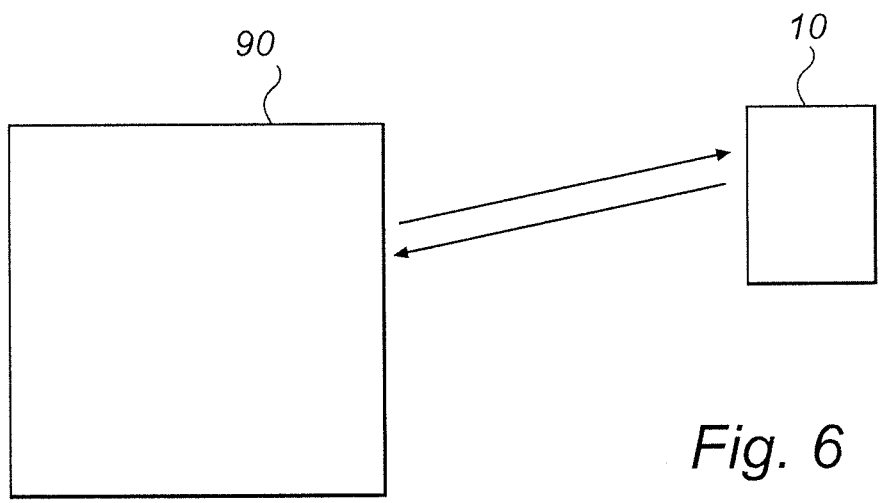
FIG. 6 is schematic diagram illustrating an embodiment of the present invention.
Figure 7:
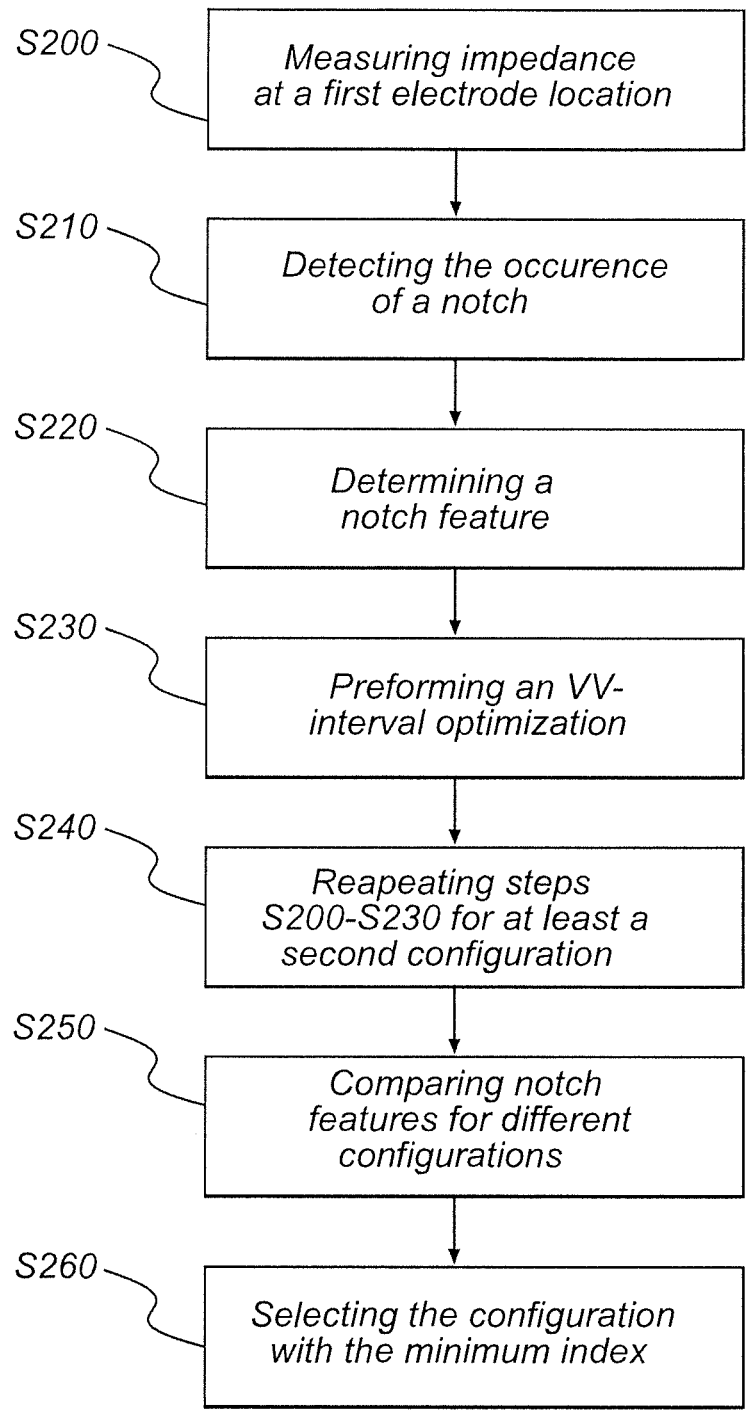
FIG. 7 is a flow chart showing the general principles for an embodiment of the method according to the present invention.

According to another aspect of the present invention, an optimization procedure so as to find or identify the optimal lead and/or electrode location can be performed. For example, during an implantation of an implantable medical device according to the present invention, a physician can perform such an optimization. In such a case, an external programmer unit 90, with reference to FIG. 6, can be connected, e.g. wirelessly or via cable, to the implantable medical device 10 to allow the physician to monitor and perform the optimization procedure. The bi-directional transition of information between the programmer unit 90 and the implantable medical device 10 can be executed, for example, by means of telemetry or RF via the communication unit 49 of the implantable medical device 10. Referring to FIG. 7, such a method for optimizing lead and/or electrode locations will be briefly discussed. First, at step S200, impedance signals at a first electrode configuration connectable to the impedance measuring unit 41 and interacting with the patient is measured. Then, at step 210, an occurrence of a notch is detected in the impedance signal coincident with a filling phase of a ventricle. The notch is indicated by a first positive slope change in a negative slope in a predetermined time window during a diastolic phase of a cardiac cycle, wherein a portion of the impedance signal within a time window surrounding the notch is determined to be a notch impedance curve. At step S220, a least one notch feature is determined using the notch impedance curve for the electrode configuration. Thereafter, at step 230, a degree of synchronicity is determined based on the notch feature for the electrode configuration, wherein a decreasing notch feature indicates an increased degree of synchronicity in the filling phase of the ventricles. Subsequently, at step 230, an optimization procedure is performed based on the notch feature by iteratively adjust a VV-interval so as to minimize the notch feature in the predetermined time window for the first electrode configuration. At step S240, steps S200-S230 are repeated for at least a second electrode configuration. Preferably, this is repeated for all possible or all desired electrode configurations. For example, the optimal location of left ventricle electrodes can be determined. This can be achieved by starting with determined locations for a right ventricle lead and right ventricle electrodes and successively testing different locations for the left ventricle lead and left ventricle electrodes. At each test location, an optimization of a VV interval can be performed to identify the notch feature for that particular location. Thereafter, each notch feature (i.e. the notch feature for each location) are compared to identify the overall minimum notch feature, which thus will correspond to the optimal location of the left ventricle lead and left ventricle electrode (-s). Of course, this procedure can also be performed to identify the optimal location for a right ventricular lead and right ventricular electrode (-s). Both left and right ventricular leads and electrodes can be optimized using the present invention. For example, a first location of the right ventricle lead and electrodes can be selected and a number of different left ventricle lead and electrode locations can be tested to identify the minimum notch feature. Then, a second location of the right ventricle lead and electrodes can be selected and all locations of the left ventricle lead are tested again to identify a minimum notch feature for this location. This is repeated for all possible locations of the right ventricle lead and electrodes. Consequently, a matrix of minimum notch features is obtained, and the overall minimum notch feature can be selected, which will correspond to the optimal locations for left and right ventricular leads and electrodes. However, the method according to this further aspect may also be used within an implanted medical device to optimize an electrode configuration if the leads comprise a number of possible electrode configurations. When all possible locations or all desired locations have been tested, at step S250, the minimum notch feature for each configuration is compared to identify an overall minimum notch feature. Then, at step S260, the electrode configuration being associated with the minimum notch feature is selected as the optimal electrode configuration or the optimal lead location.

According to yet another embodiment of the present invention, a pacing analyzer for optimizing lead and/or electrode locations is connectable to at least one medical lead implantable in a heart of a patient. A pacing analyzer is used to assess the electrical performance of a lead system during implantation of a heart stimulator, e.g. a stimulator as described above with reference to FIGS. 2 and 3, or invasive lead-system trouble shooting. The analyzer includes a pace pulse generator adapted to produce cardiac stimulating pacing pulses and being connectable to at least one medical lead for delivering stimulation pulses to cardiac tissue of the heart, an impedance measuring unit adapted to, during impedance measuring sessions, measure impedance signals obtained at an electrode configuration and/or lead configuration being located at the right side of the heart, wherein the electrodes of the electrode configuration are connectable to the device. Further the analyzer includes a notch detecting unit adapted to detect an occurrence of a notch in the impedance signal coincident with a filling phase of a ventricle during the change from rapid filling to slow filling, the notch being indicated by a first positive slope change in a negative slope in a predetermined time window during a diastolic phase of a cardiac cycle, wherein a portion of the impedance signal within a time window surrounding the notch being a notch impedance curve, a notch feature determining unit adapted to determine notch feature using the notch impedance curve, and a synchronicity determining unit adapted to determine a degree of synchronicity based on the notch feature, wherein a decreasing notch feature indicates an increased degree of synchronicity in the filling phase of the ventricles. Further, the pacing analyzer comprises a VV delay determining unit adapted to perform an optimization procedure, wherein the pace pulse generator is controlled to, based on the notch feature, iteratively adjust a VV-interval so as to minimize the notch feature in the predetermined time window, and a control unit adapted to: compare the minimum notch feature for different electrode and/or lead configurations to identify a overall minimum notch feature; and indicate the electrode configuration being associated with the minimum notch feature. Thus, a physician can use the pacing analyzer to optimize lead and/or electrode locations during, for example, implantation. First, the pacing analyzer is connected to the medical lead or leads. Then, impedance signals at a first electrode configuration located such that the impedance signals substantially reflects ventricular wall movements are measured during change from rapid filling to slow filling. Then, the occurrence or existence of a notch is detected in the impedance signals, which may be differentiated impedance signals. A notch feature is determined and a degree of synchronicity is determined based on the notch feature. Thereafter, an optimization procedure is performed based on the notch feature by iteratively adjust a VV-interval so as to minimize the notch feature for the first electrode configuration. Further, the preceding steps are repeated for at least a second electrode configuration. Preferably, this is repeated for all possible or all desired electrode configurations. For example, the optimal location of left ventricle electrodes can be determined. This can be achieved by starting with determined locations for a right ventricle lead and right ventricle electrodes and successively testing different locations for the left ventricle lead and left ventricle electrodes. At each test location, an optimization of a VV interval can be performed to identify the minimum notch feature for that particular location. Thereafter, each notch feature (i.e. the notch feature for each location) are compared to identify the overall minimum notch feature, which thus will correspond to the optimal location of the left ventricle lead and left ventricle electrode (-s). Of course, this procedure can also be performed to identify the optimal location for a right ventricular lead and right ventricular electrode (-s). Both left and right ventricular leads and electrodes can be optimized using the present invention. For example, a first location of the right ventricle lead and electrodes can be selected and a number of different left ventricle lead and electrode locations can be tested to identify the minimum notch feature. Then, a second location of the right ventricle lead and electrodes can be selected and all locations of the left ventricle lead are tested again to identify a minimum notch feature for this location. This is repeated for all possible locations of the right ventricle lead and electrodes. Consequently, a matrix of minimum notch features is obtained, and the overall minimum notch feature can be selected, which will correspond to the optimal locations for left and right ventricular leads and electrodes. However, the method according to this further aspect may also be used within an implanted medical device to optimize an electrode configuration if the leads comprise a number of possible electrode configurations. When all possible locations or all desired locations have been tested, the minimum notch feature for each configuration is compared to identify an overall minimum notch feature. Then, the electrode configuration being associated with the minimum notch feature is selected as the optimal electrode configuration or the optimal lead location.

Although modifications and changes may be suggested by those skilled in the art, it is the intention of the inventor to embody within the patent warranted heron all changes and modifications as reasonably and properly come within the scope of her contribution to the art.

I claim as my invention:

1. An implantable medical device for monitoring ventricular synchrony of a heart of patient including a pace pulse generator adapted to produce cardiac stimulating pacing pulses and being connectable to at least one medical lead for delivering bi-ventricular pulses to cardiac tissue of said heart, comprising:
    an impedance measuring unit that during impedance measuring sessions, measures an impedance signal using an electrode configuration, said configuration being connectable to said impedance measuring unit and interacting with said patient;
    a notch detecting unit that detects an occurrence of a notch in the impedance signal coincident with a period including a change from rapid to slow filling of a ventricle, said notch being indicated by a first positive slope change in a negative slope in a predetermined time window during a diastolic phase of a cardiac cycle, wherein a portion of the impedance signal within a time window surrounding said notch being a notch impedance curve;
    a notch feature determining unit that determines a notch feature using said notch impedance curve;
    a synchronicity determining unit that determines a degree of synchronicity based on said notch feature, wherein a decreasing notch feature indicates an increased degree of synchronicity in the filling phase of the ventricles; and
    a VV delay determining unit adapted to perform an optimization procedure, and wherein said pace pulse generator is controlled to, based on said notch feature, iteratively adjust a VV-interval so as to minimize said notch feature to obtain substantially synchronized ventricle contractions.

2. The implantable medical device according to claim 1, wherein said notch detecting unit detects the notch as the first positive slope change in the negative slope in the predetermined time window during the diastolic phase of the cardiac cycle, wherein said predetermined time window starting a predetermined period of time from the end of the systolic phase.

3. The implantable medical device according to claim 1, wherein said notch feature determining unit that calculates a first derivative of the measured impedance signal, said notch being indicated by the first positive slope change after a zero derivative of said impedance signal.

4. The implantable medical device according to claim 3, wherein said notch feature determining unit determines the notch feature based on:
    a notch start point, said notch start point being measured from the first point of a second zero derivative of said impedance signal after a T-wave;
    a notch width, said notch width being determined to be a distance from the notch to the first point of a third zero derivative after the notch;
    a notch area, said notch area being determined to be an area of the differentiated notch impedance curve between the notch and the first point of the third zero derivative after the notch or between two intersection points of the differentiated notch impedance curve and a threshold relative to the maximum of the derivate derivative of the notch impedance cure.

5. The implantable medical device according to claim 1, comprising a breath rate sensor that senses a breathing cycle of said patient, and wherein said notch feature determining unit determines said notch feature in synchronism with an event of said a breathing cycle of said patient or as an average value over a predetermined number of breathing cycles.

6. The implantable medical device according to claim 1 comprising a body posture sensor that senses a body posture of said patient, and wherein said notch feature determining unit determines said notch feature in synchronism with a predetermined body posture of said patient, or as an average value of the notch feature of at least two body postures.

7. The implantable medical device according to claim 1, wherein said notch feature determining unit determines a shape of notch impedance curve to be said notch feature.

8. The implantable medical device according to claim 7, further comprising a VV delay determining circuit that performs an optimization procedure, and wherein said pace pulse generator is controlled to, based on said notch feature, iteratively adjust a VV-interval so as to obtain a smooth notch impedance curve.

9. The implantable medical device according to claim 1, wherein said synchronicity detecting unit compares said notch feature with a reference notch feature to obtain a comparison result and to determine the degree of synchronicity based on said comparison result.

10. The implantable medical device according to claim 9, wherein said synchronicity detecting unit executes a pattern comparison with a reference impedance curve to obtain said comparison result and to determine the degree of synchronicity based on said comparison result.

11. The implantable medical device according to claim 1, further comprising an IEGM detecting unit that senses IEGM signals for consecutive cardiac cycles of said heart and that detects cardiac events in said IEGM signals, and wherein said notch detecting unit detects the occurrence of a notch within said predetermined time window, said time window having a predetermined length of time and starting a predetermined period of time after the detection of a T-wave in an IEGM signal corresponding to a cardiac cycle.

12. The implantable medical device according to claim 1, wherein said impedance signal is measured using an electrode configuration including at least a first pair of electrodes having a ring electrode and a tip electrode arranged in a medical lead located in the right ventricle, or a first electrode located adjacent to the septum in the right ventricle and a second electrode located in a coronary vein on the left ventricle.

13. A method for monitoring ventricular synchrony of a heart of a patient in an implantable medical device including a pace pulse generator that emits cardiac stimulating pacing pulses and is connectable to at least one medical lead for delivering bi-ventricular pulses to cardiac tissue of said heart, comprising: during impedance measuring sessions, measuring an impedance signal using an electrode configuration being connectable to an impedance measuring unit and interacting with said patient, and generating a corresponding impedance signal;
    detecting an occurrence of a notch in the impedance signal coincident with a period including a change from rapid to slow filling of a ventricle, said notch being indicated by a first positive slope change in a negative slope in a predetermined time window during a diastolic phase of a cardiac cycle, wherein a portion of the impedance signal within the time window surrounding said notch being a notch impedance curve;
    determining a notch feature using said notch impedance curve;
    determining a degree of synchronicity based on said notch feature, wherein a decreasing notch feature indicates an increased degree of synchronicity in the filling phase of the ventricles; and performing an optimization procedure based on said notch feature by iteratively adjusting a VV-interval so as to minimize said notch feature to obtain substantially synchronized ventricle contractions.

14. The method according to claim 13, wherein said detecting includes detecting the notch as the first positive slope change in the negative slope in the predetermined time window during the diastolic phase of the cardiac cycle, wherein said predetermined time window starts a predetermined period of time from the end of the systolic phase.

15. The method according to claim 13, wherein said determining includes calculating a first derivative of the measured impedance signal, said notch being indicated by the first positive slope change after a zero derivative of said impedance signal.

16. The method according to claim 15, wherein said determining includes determining the notch feature based on:
   a notch start point, said notch start point being measured from the first point of a second zero derivative of said impedance signal after a T-wave;
   a notch width, said notch width being determined to be a distance from the notch to the first point of a third zero derivative after the notch; and
   a notch area, said notch area being determined to be an area of the differentiated notch impedance curve between the notch and the first point of the third zero derivative after the notch or between two intersection points of the differentiated notch impedance curve and a threshold relative to the maximum of the derivate derivative of the notch impedance curve.

17. The method according claim 13, further including sensing a breathing cycle of said patient and determining said notch feature in synchronism with an event of said breathing cycle of said patient or as an average value over a predetermined number of breathing cycles.

18. The method according to claim 13, further comprising sensing a body posture of said patient and determining said notch feature in synchronism with a predetermined body posture of said patient, or as an average value of the notch feature of at least two body postures.

19. The method according to claim 13, wherein said determining includes determining a shape of notch impedance curve to be said notch feature.

20. The method according to claim 19, further comprising performing an optimization procedure based on said notch feature by iteratively adjusting a VV-interval so as to obtain a smooth notch impedance curve.

21. The method according to claim 13, further comprising comparing said notch feature with a reference notch feature to obtain a comparison result and to determine the degree of synchronicity based on said comparison result.

22. The method according to claim 21, further comprising implementing a pattern comparison with a reference impedance curve to obtain a comparison result to determine the degree of synchronicity based on said comparison result.

23. The method according to claim 13, further comprising sensing IEGM signals for consecutive cardiac cycles of said heart and to detect cardiac events in said IEGM signals and detecting the occurrence of a notch within said predetermined time window, said time window having a predetermined length of time and starting a predetermined period of time after the detection of a T-wave in an IEGM signal corresponding to a cardiac cycle.

24. The method according to claim 13, further comprising measuring the impedance using an electrode configuration including at least a first pair of electrodes having a ring electrode and a tip electrode arranged in a medical lead located in the right ventricle, or a first electrode located adjacent to the septum in the right ventricle and a second electrode located in a coronary vein on the left ventricle.

25. A method for optimizing lead and/or electrode locations, said comprising a plurality of electrodes being connectable to an implantable medical device comprising a pace pulse generator that emits cardiac stimulating pacing pulses and is connectable to at least one medical lead for delivering stimulation pulses to cardiac tissue of a heart, comprising:
   a) measuring an impedance signal at a first electrode configuration, wherein the electrodes of said electrode configuration are connectable to said implantable medical device and are located at a right side of said heart;
   b) detecting an occurrence of a notch in the impedance signal coincident with a period including a change from rapid to slow filling of a ventricle, said notch being indicated by a first positive slope change in a negative slope in a predetermined time window during a diastolic phase of a cardiac cycle, wherein a portion of the impedance signal within the time window surrounding said notch being a notch impedance curve;
   c) determining a notch feature using said notch impedance curve for said electrode configuration;
   d) determining a degree of synchronicity based on said notch feature for said electrode configuration, wherein a decreasing notch feature indicates an increased degree of synchronicity in the filling phase of the ventricles;
   e) performing an optimization procedure based on said notch feature by iteratively adjusting a VV-interval so as to minimize said notch feature in said predetermined time window for said first electrode configuration to determine a minimum notch feature;
   f) repeating (a)-(e) for at least a second electrode configuration;
   g) comparing said minimum notch feature for each configuration to identify an overall minimum notch feature; and
   h) selecting the electrode configuration being associated with the minimum notch feature.

26. A system for optimizing lead and/or electrode locations including a plurality of electrodes and an implantable medical device, said system comprising:
   at least one medical lead arrangement comprising said plurality of electrodes in an electrode configuration;
   a pace pulse generator that produces cardiac stimulating pacing pulses and is connected to said at least one medical lead arrangement for delivering stimulation pulses to cardiac tissue of a heart of a patient;
   an impedance measuring unit that, during impedance measuring sessions, measures an impedance signal obtained at the electrode configuration connected to said impedance measuring unit and interacting with said patient, wherein the electrodes of said electrode configuration are located at a right side of said heart;
   a notch detecting unit that detects an occurrence of a notch in the impedance signal coincident with a period including a change from rapid to slow filling of a ventricle, said notch being indicated by a first positive slope change in a negative slope in a predetermined time window during a diastolic phase of a cardiac cycle, wherein a portion of the impedance signal within a time window surrounding said notch being a notch impedance curve;
   a notch feature determining unit that determines a notch feature using said notch impedance curve;
   a synchronicity determining unit that determines a degree of synchronicity based on said notch feature; and an external control unit in connection with said implantable medical device and being configured to:
instruct said implantable medical device to obtain a notch feature for at least a second electrode configuration;
compare said notch feature for each configuration to identify a minimum notch feature; and
select the electrode configuration being associated with the minimum notch feature.

27. A pacing analyzer for optimizing lead and/or electrode locations being connectable to at least one medical lead implantable in a heart of a patient and defining at least one medical lead arrangement comprising electrodes in an electrode configuration, said analyzer comprising:
a pace pulse generator that emits cardiac stimulating pacing pulses and connected to said at least one medical lead arrangement for delivering stimulation pulses to cardiac tissue of a heart of a patient;
an impedance measuring unit that, during impedance measuring sessions, measures an impedance signal obtained at the electrode configuration connected to said impedance measuring unit and interacting with said patient, wherein the electrodes of said electrode configuration are located at a right side of said heart;
a notch detecting unit that detects an occurrence of a notch in the impedance signal coincident with a period including a change from rapid to slow filling of a ventricle, said notch being indicated by a first positive slope change in a negative slope in a predetermined time window during a diastolic phase of a cardiac cycle, wherein a portion of the impedance signal within a time window surrounding said notch being a notch impedance curve;
a notch feature determining unit that determines a notch feature using said notch impedance curve;
a synchronicity determining unit that determines a degree of synchronicity based on said notch feature, wherein a decreasing notch feature indicates an increased degree of synchronicity in the filling phase of the ventricles;
a VV delay determining unit that executes an optimization procedure, wherein said pace pulse generator is controlled to, based on said notch feature, iteratively adjust a VV-interval so as to minimize said notch feature in said predetermined time window to determine a minimum notch feature; and
a control unit configured to:
compare said minimum notch feature for different electrode and/or lead configurations to identify an overall minimum notch feature; and
indicate the electrode configuration being associated with the overall minimum notch feature.

* * * * *